United States Patent [19]

Capiau et al.

[11] Patent Number: 5,391,715
[45] Date of Patent: Feb. 21, 1995

[54] **METHOD FOR ISOLATING AND PURIFYING BORDETELLA *PERTUSSIS* ANTIGENIC FACTORS**

[75] Inventors: Carine Capiau, Harveng Mons; Pierre Desmons, Nivelles, both of Belgium

[73] Assignee: SmithKline Beecham Biologicals, Rixensart, Belgium

[21] Appl. No.: 856,817

[22] Filed: Mar. 24, 1992

Related U.S. Application Data

[63] Continuation of Ser. No. 693,213, Apr. 30, 1991, abandoned, which is a continuation-in-part of Ser. No. 431,999, Nov. 6, 1989, abandoned.

[51] Int. Cl.$^6$ .......................... C07K 3/02; C07K 3/20; C07K 15/04
[52] U.S. Cl. .................................. 530/396; 530/415; 530/417; 530/825
[58] Field of Search .................. 424/92; 530/350, 396, 530/415, 417, 825

[56] References Cited

U.S. PATENT DOCUMENTS

| | | | |
|---|---|---|---|
| 4,563,303 | 1/1986 | Ginnaga et al. | 530/417 |
| 4,784,589 | 11/1988 | Robinson et al. | 530/417 |
| 4,997,915 | 3/1991 | Tan et al. | 530/380 |

FOREIGN PATENT DOCUMENTS

| | | |
|---|---|---|
| 0121249A2 | 10/1984 | European Pat. Off. |
| 0140386A2 | 5/1985 | European Pat. Off. |
| 0231083A2 | 8/1987 | European Pat. Off. |

OTHER PUBLICATIONS

Y. Sato, et al., *The Lancet*, Jan. 21, 1984, pp. 122–126.
M. Christodoulides, et al., *Vaccine*, vol. 5, Sep. 1987, pp. 199–207.
M. Svoboda, et al., *Analytical Biochemistry*, 159:402–411 (1986).
R. D. Sekura, et al., *J. Biol. Chem.*, 258:14647–14651 (1983).
Y. Sato, et al., *Infection and Immunicty*, vol. 41, No. 1, Jul. 1983, pp. 313–320.
M. Chazono, et al., *J. Biol. Standardization*, 16:83–89 (1988).
J. J. Munoz, et al., *Infection and Immunity*, vol. 32, No. 1, Apr. 1981, pp. 243–250.
Chem. Abstract 102(9):77281z (1985) (equivalent to JP 59175439A).
*Fundamentals of Biotechnology*, Prave et al, eds. VCH. 1987. p. 311.

*Primary Examiner*—Jeffrey E. Russel
*Attorney, Agent, or Firm*—Jeffrey A. Sutton; Herbert H. Jervis; Edward T. Lentz

[57] ABSTRACT

A process is provided for the purification of pertussis toxin (PT) and/or filamentous hemagglutinin antigen (FHA) from a *B. pertussis* fermentation broth or cell free culture supernatant containing at least one antigen, which comprises contacting the fermenation broth or cell free culture supernatant with a hydroxyapatite adsorbent for a sufficient time to adsorb the antigen(s) at a pH which both PT and FHA are adsorbed and eluting a mixture containing the adsorbed antigen(s) from the adsorbent with eluant at a pH which both PT and FHA are eluted. The PT and FHA may be further purified by two sequential chromatographic columns, one of which involves apolar-ligand chromatography.

21 Claims, 4 Drawing Sheets

Fig. 4 ns. For example, U.S. Pat. No. 4,563,303 refers to
METHOD FOR ISOLATING AND PURIFYING BORDETELLA *PERTUSSIS* ANTIGENIC FACTORS This is a continuation of application Ser. No. 07/693,213, filed Apr. 30, 1991, now abandoned, which is a continuation-in-part of Ser. No. 07/431,999, filed Nov. 6, 1989, now abandoned.

TECHNICAL FIELD

The present invention relates generally to components for a vaccine against whooping cough. More specifically, the invention provides a process for isolating and purifying antigenic factors from *Bordetella pertussis* in high yield and in a pure and stable form, the purified factors and mixtures thereof.

BACKGROUND OF THE INVENTION

Whooping Cough, or pertussis, is a highly infectious disease which primarily affects children. In addition to causing respiratory complications, whooping cough may result in nerve damage and high mortality, particularly in children in low socioeconomic groups and in newborn infants without maternal anti-pertussis antibodies. The etiologic agent of pertussis is the gram negative coccobacillus *Bordetella pertussis*. The bacteria is believed to invade the respiratory tract and induce a toxic state which remains even after the disappearance of the bacteria.

Although world health organizations presently recommend the immunization of infants to prevent the incidence and spread of pertussis, great concern has arisen over the negative effects of various vaccine forms. The toxicity of conventional *B. pertussis* vaccine formulations causes side effects which vary from simple flushing to permanent neurological damage and/or death. Consequently, reduced use of conventional *B. pertussis* vaccines has resulted in an increase in the number of pertussis cases.

The most widely used vaccine contains whole, *B. pertussis* organisms, which are inactivated after treatment at 56° C. for 30 minutes. Since the bacteria are not subjected to any other detoxification treatment, any toxic substance which can withstand the elevated temperature is included in the vaccine and contributes to the occurrence of side effects. Another consequence of this type of vaccine is the formation of a broad spectrum of antibodies as a response upon administration. The sera induced by such vaccines lack high specificity and high protecting potential for use as preventive or therapeutic treatments, and have no value at all as diagnostic materials.

Other pertussis vaccines are prepared from culture supernatant of *B. pertussis*. However, variabilities in cultivation allow the final composition of the microorganism to vary, and the inactivating agents, glutaraldehyde or formaldehyde, occasionally lead to aggregated materials subject to conversion to active toxic substances upon storage.

Alternate vaccines are prepared from avirulent or toxin deficient Strains. However, these vaccines have proven to be much less protective than those prepared from virulent strains. See Wardlaw et al, *J. Med. Micro. Biol.*, 9:89–100 (1976).

To avoid the side effects caused by whole cell vaccines, research turned to the investigation of the toxic components of the *B. pertussis* bacteria for use in acellular vaccines. One important component is pertussis toxin (PT), a protein exotoxin which plays a major role in the pathogenesis of whooping cough and is believed to be the major protective antigen of *B. Pertussis*. [A. A. Weiss et al, *Ann. Rev. Microbiol.*, 40:661 (1986)].

Another component of interest for an acellular *B. pertussis* vaccine is the antigen, filamentous hemagglutinin (FHA). This antigen, alone or in combination with PT, has been noted to have some protective capacity. See, e.g., U.S. Pat. No. 4,563,303 and European patent application 231,083.

Purification procedures to isolate the PT and FHA antigens from whole cell *B. pertussis* have been published resulting in varied yields, and purity of components. For example, U.S. Pat. No. 4,563,303 refers to purifying FHA from Bordetella by adsorbing it on a cellulose sulfate, polysaccharide gel bound with dextran sulfate or a cross-linked polysaccharide gel, and eluting FHA therefrom.

J. J. Munoz et al, *Inf. Immun.*, 32:243–250 (1983) and Japanese published application 59.175439A refer to separate fermentation procedures for each of the two factors PT and FHA and a culture medium for production of FHA. The separation and purification methods described in these documents involve laborious and time-consuming extractions, precipitations, centrifugations and dialysis, followed by a chromatographic purification. Such processes demand at least a week for the isolation of a single factor and are clearly unsatisfactory for antigen or vaccine production on a commercial scale.

M. Chazono et al, *J. Biol. Stand.*, 16:83–89 (1988) and European patent application 121,249 refer to PT and FHA, as major substances of the total hemagglutinin fraction excreted by *B. pertussis* for use in a vaccine formulation in the same ratio as they occur in fermentation broth. For the extraction and purification of the hemagglutinin the fermentation broth was centrifuged to separate off the cell mass, followed by ammonium sulphate mediated precipitation from the supernatant. The precipitate was purified after redissolution via a sucrose density centrifugation, followed by separation and dialysis. The techniques employed in this method involve manipulations of large volumes requiring complex and sophisticated apparatus, such as continuous centrifugation to avoid lengthy exposure to open air and laborious and frequent manipulations. This results in batch to batch variations of the antigenic composition of the product. Finally, the purity of the resulting antigens may still be insufficient due to residual endotoxins and pyrogenicity caused by lengthy exposure to open air.

Y. Sato et al., *Infect. Immun.*, 41:313–320 (1983) describe a purification method employing primarily affinity chromatography. In this system fermentation broth is passed over spheroidal hydroxyapatite at pH of about 8, whereby most of the FHA is adsorbed, while PT is eluted. Centrifugation prior to the filtration over the adsorbent avoids blocking of the adsorbent by cells and debris, which cause poor flow behavior, poor recovery, slow operation and undesirable contamination for the subsequent steps. The eluate containing the PT fraction is then adjusted to a pH of about 6 and passed over another hydroxyapatite column, whereby PT is retained. Both factors are then further treated in fully separate systems. In this procedure both factors, after elution from their hydroxyapatite carrier with an appropriate buffer/salt solution and pooling, are passed over a support modified with an affinity ligand as haptoglobin sepharose or fetuin-sepharose, to which PT is selectively bound while FHA remains unaffected. The purification is then completed by precipitation, and/or another simple chromatographic fractionation and/or dialysis.

R. D. Sekura et al, *J. Biol. Chem.*, 258:14647-14651 (1983) describes an analogous method, restricted to PT alone. In this procedure the extraction from the supernatant obtained by centrifugation of a *B. pertussis* fermentation broth is accomplished by adding Affi-Gel blue resin in batch to the supernatant at pH 6, separating it from the liquid phase after a contact time of about two days, eluting the PT that has bound specifically to the Cibacron dye (because of its NAD like structure), with an appropriate buffer/salt solution and pooling the active fractions. For the first purification fetuin-agarose is used as affinity support to bind PT selectively; after elution the purification is completed with a simple fractionating chromatography and salting out.

While the chromatographic methods of Sato et al and Sekura et al avoid the very labor intensive and time consuming zonal centrifugation, they still require separation of cells and debris from the fermentation broth. The adsorption from the supernatant in batch, without passing the whole liquid over a chromatographic column as described in Sekura et al, is a practical simplification. However, in that method there is only one target component to be isolated.

Another chromatographic purification of PT alone was reported by M. Svoboda et al, *Anal. Biochem.*, 159:402-411 (1986). PT was adsorbed from the culture supernatant by adding Blue Sepharose (an equivalent to other Cibacron modified supports) in batch for about 12 hours at pH 6.0, filtering the adsorbent and packing it into a chromatographic column. After elution and pooling the PT fraction was immediately loaded on a Phenyl-Sepharose carrier, to which PT, because of its hydrophobic character, and because of the high ionic strength of the medium, was bound. Elution was accomplished with a pH 10 buffer/glycerol mixture at relatively low salt concentration. The pooled fractions were diluted and acidified to pH 5.0, loaded on hydroxyapatite HTP, and separated from remaining PT-fragments by eluting and pooling.

M. Christodoulides et al, *Vaccine*, :199-207 (1987) refer to the extraction of PT and FHA from *B. pertussis* culture using dye-ligand chromatography based on the Sekura et al procedure. The pH of the culture fluid was adjusted to 6.0 and Blue Sepharose gel was added. The gel was washed with Tris-HCl, pH 8.0 buffer and bound material eluted with the buffer containing 1.0M NaCl, pH 8.0.

Y. Sato et al, *Lancet*, pp. 122-126 (Jan. 21, 1984) refer to a pertussis component vaccine prepared by salting out the FHA antigen and LPF-HA antigen in a *B. pertussis* culture by fractional precipitation, extraction in phosphate; fractionation by ultracentrifugation; pooling of HA fractions; detoxification with formalin; and addition of adjuvant.

Still other purification techniques employ supports for the selective adsorption of PT from a *B. pertussis* culture supernatant. European Patent Application 140386A refers to the use of denatured human or animal ceruloplasmin as an affinity ligand which may be bound to CNBr activated sepharose, agarose, cellulose or dextran.

The availability of the affinity supports in larger quantities and with a constant and certified quality however remains a major drawback to large scale commercial use of presently available purification methods. This type of support cannot be sterile and therefore always carries the inherent risk of contamination, especially with viruses, unacceptable in production of human medical products.

There remains a continuing need in the art for effective and safe vaccines against whooping cough, as well as convenient diagnostic tools for early detection of *B. pertussis* infection.

SUMMARY OF THE INVENTION

In one aspect the present invention provides an improved process for a fast, simple and safe extraction of highly purified *B. pertussis* antigenic factors from a fermentation broth of *B. pertussis*. Desirably the factors extracted are pertussis toxin (PT) and/or filamentous hemagglutinin (FHA).

This process involves contacting a whole fermentation broth or cell free culture supernatant containing one or both of these *B. pertussis* antigens with a hydroxyapatite-containing adsorbent capable of adsorbing both antigens. This adsorbent, after a suitable contact time with the broth, is then separated from the broth. A solution containing partially purified PT and/or FHA is thereafter eluted from the adsorbent under suitable conditions of pH, ionic strength and temperature.

This process produces these factors at good yields and in a concentrated and partially purified form which can easily be sterilized by filtration through microporous membranes. When applied to whole fermentation broth, the process avoids the need for centrifugation to effect the removal of bacterial cells to obtain a cell-free culture supernatant.

Another aspect of the present invention involves a modification of the above method, permitting further purification of the PT and/or FHA containing solution. In addition to the method described above, additional steps following the extraction procedures of the invention permit further purification of one or more of the antigenic factors. These additional steps involve exposing the solution described above to two sequential column chromatographic procedures. One of the chromatographies employs an apolar ligand chromatographic column. Preferably the apolar ligand chromatography is the first of the two procedures. Elution of the partially purified mixture of PT and FHA from these two columns produces a purified mixture of the antigens in a form essentially free of endotoxins and other proteinaceous materials.

In yet a further aspect of this invention the PT and FHA factors in the mixture resulting from the above purification method steps can easily be separated from each other without mutual contamination by the application of a conventional size exclusion chromatography step.

This modified method of the invention allows the PT or FHA factors to be produced in good yield at a quality level acceptable for use as immunogenic factors or precursors for human administration. Additionally, the process may be readily adapted to industrial production scale.

In still a further aspect, the present invention provides highly purified *B. pertussis* antigenic factors, more specifically PT and FHA, in large quantities produced by the processes of the present invention. These factors enable the development of safe, potent and stable component vaccines against *B. pertussis*, whether the factors are employed individually or as a mixture together with vaccines against other organisms, viruses or diseases. These purified factors provide the basic materials for the production of anti-*B. pertussis* sera, useful in the preventive, diagnostic or therapeutic treatment of *B. pertussis* infection.

Other aspects and advantages of the present invention are described further in the following detailed description of preferred embodiments of the present invention.

DETAILED DESCRIPTION OF THE INVENTION

The present invention provides improved methods for the extraction and purification from a fermentation broth or culture of *B. pertussis* of one or more antigenic factors. Particularly provided by this invention are purification methods for the factors, PT and/or FHA. Also provided by this invention are mixtures of purified PT and FHA antigens, and purified forms of the individual antigens.

One method of the present invention provides for the extraction of PT and/or FHA from a fermentation broth or culture of *Bordetella pertussis*. Various strains of *B. pertussis* for use in the methods of this invention are described and readily available in commercial collections, such as the American Type Culture Collection, Rockville, Md. Any of these available strains may be used in the processes of the present invention, provided they are capable of producing at least one, and preferably both, of the desired antigenic factors, PT and FHA, in adequate amounts in a liquid culture medium.

Examples of strains that may be employed in the present invention include, without limitation, *B. pertussis* phase I, *B. pertussis* phase II, *B. pertussis* phase I CS, *B. pertussis* Tohama, *B. pertussis* strain 185-30, *B. pertussis* strain 18-323, *B. pertussis* strain 134, *B. pertussis* strain 509, *B. pertussis* strain Wellcome 28, and Office of Biologics *B. pertussis* strain 165. A preferred strain for use in the present invention is *B. pertussis* phase I, Tohama, which is available from the Institute of Fermentation, Osaka, Japan, under accession number IFO-14073.

For use in the present invention the selected *B. pertussis* strain can be grown in a variety of ways known to one of skill in the art. Various cultivation methods are known which employ different cultivation steps, and liquid or solid media, depending on the quantity and origin or conservation method of the seed culture. However, any known method will suffice for use in the present invention which provides an inoculum of a conventionally-acceptable size for large scale production.

A suitable medium for growth of a *B. pertussis* inoculum may be selected by one of skill in the art including, without limitation, Gengou medium [EPA 82/305465.5.]; the media described in N. Andorn et al, *Appl. Microbiol. Biotechnol.*, 28:356-360 (1988) and references cited therein; Verway medium [U.S. Pat. No. 4,784,589]; synthetic medium B2 [P. Van Hemert, in Prog. Indust. Microbiol., (Bull, M. J., ed), vol. 13, p. 151, Elsevier Sci., Amsterdam (1977)] or described modifications thereof.

For growth of the *B. pertussis* culture, which is the starting material of the present invention, an inoculum is added to a suitable liquid medium and fermentation is conducted employing conventional fermentation methods and fermentor designs known in the art. Those of skill in the art will appreciate that different results may be obtained depending upon the selection of a particular combination of conventional fermentor design, fermentation medium, method and parameters. Preferred combinations for use in the present invention are those suitable for use in large-scale production. Examples of such combinations of methods, designs and media are exemplified in EPA 077,646; EPA 121,249; EPA 239,504; Andorn et al, Sato et al (1983), Sekura et al and Svoboda et al, all cited above, and incorporated by reference herein. The methods described in EPA 121,249; Andorn et al, cited above, and EPA 239,504 are most preferred.

In the practice of this invention, after completion of fermentation, the *B. pertussis* fermentation broth is maintained in a sterile condition to avoid denaturation and/or degradation of the desired PT or FHA factors. The two antigens are extracted in a temperature range between 1° and 25° C. In a preferred embodiment of the invention the broth is cooled to 1°-10° C. and held at this temperature. The pH is adjusted to below 7.0. Preferably the pH is adjusted to a range of between about pH 6.0 and pH 6.4 with phosphoric or acetic acid. A preservative can optionally be added to the broth. For example, sodium thimerosal may be added to the broth to a final concentration of up to 0.2 g/l or 2-phenoxyethanol may be added to the broth to a final concentration of between 0.3% to 1%. If desired, a conventional preservative may be also added to the buffer solutions used in the processes of this invention.

As an optional first step in the method of the invention, the fermentation broth can be passed over a filter to remove major particles and pellets therefrom, provided that contact is avoided with contamination risks from the environment.

According to the method, hydroxyapatite (HO-apa) is added to the fermentation broth in a form suitable to sediment more easily than the cells or small cell particulates in the broth. In a preferred embodiment, the method of the invention employs physical means or additional process steps to facilitate separation of the HO-apa from the total culture liquid, and to minimize the contact time between the liquid and the adsorbent. For example, the adsorbent may be introduced into the culture broth in a porous or semipermeable support or carrier. In one such preferred embodiment the HO-apa is in crystalline form or is bound, adsorbed on or entrapped in a supporting material which provides the HO-apa particles with a specific density sufficiently different from the density of most particles in the original culture broth. Preferred forms of the HO-apa adsorbent have an apparent density equal or higher than 1.15 to facilitate separation of the HO-apa/adsorbed PT and FHA from the liquid by conventional means.

In another preferred embodiment of the invention the HO-apa adsorbent is carried on a support which enhances the granulometry, porosity and mechanical properties of the adsorbent. Preferred supports have a granule size of 60 μm or larger, and a pore size allowing diffusion of both antigens, corresponding to an exclusion limit of 300 KDa or greater. Such adsorbents may be obtained by entrapping HO-apa in, or binding or adsorbing HO-apa on, sufficiently porous and rigid structures compatible with the culture medium. Such supports include, without limitation, silica, alumina and other common inorganic porous supports, or organic resins, or bio-organic gelling supports, as acrylic, vinylic, agarose, cellulose or a mixture. These supports can be eventually structurized or rigidised by crosslinking. A number of desirable supports are commercially available, such as HA-Utrogel [IBF, France] or HA-TSK-Gel, HA Type [TOYO 500 Mfg. Co., Japan]. These supports enable good flow characteristics and sufficient separating power, with a maximal adsorbing capacity for the desired biological factors. The use of HO-apa carried on these supports facilitates the packing and washing of the support in a chromatographic column, and the subsequent elution of the desired factors. It is also preferred that the adsorbent be sterile for use in the present invention.

According to the practice of the present invention the HO-apa adsorbent is added to the *B. pertussis* culture broth in a minimum amount of at least 0.5 grams HO-apa per liter of the culture liquid. A preferred quantity of HO-apa ranges from 0.5–2.0 grams HO-apa per liter of the culture liquid.

The adsorbent is then left in contact with the culture liquid for sufficient time to allow a nearly complete adsorption of the desired components on the adsorbent. Generally, the time for complete adsorption can range from 5 minutes to 30 hours. More preferably the time for adsorption is between 6 to 24 hours, usually overnight. During the adsorption time, the culture broth is preferably gently stirred. Mechanical means such as stirring or pumping movements may also be employed during the adsorption time, enabling a more intense contact of the culture liquid with the adsorbent.

Following completion of adsorption, the adsorbent is separated from the bulk of the culture liquid, generally by sedimentation to the bottom of the vessel containing the culture broth. The culture liquid may optionally be transferred from the fermentor to another tank or vessel with improved capacity for separation of the adsorbent. For example, a vessel with a conical bottom allows separation after sedimentation of the adsorbent. Alternatively, a vessel permitting decantation of the culture liquid from the adsorbent after most of the desired factors have been adsorbed to the HO-apa may be employed. Selective retention of the adsorbent may be enhanced by techniques such as filtration or fluidization or centrifugation.

After separation from the bulk of the culture liquid, the absorbent is washed extensively with a buffered solution at low ionic strength between 5 and 200 mM. The buffer desirably has a pH between 5 and 8. The washing step may be performed at a temperature of approximately between 1° to 15° C. This washing step removes most remaining cells and remaining unwanted constituents of the original fermentation broth. Preferably, the washing step employs a buffer having a pH range of about 5.5 to 7 and a ionic strength of less than 150. A particularly desirable temperature for this washing is between approximately 4° to 8° C.

Buffer systems used in the present invention may be any of those commonly used for the treatment of biological factors and well known to one skilled in the art. Limitations on useful conventional buffer systems for this method are simply that the selected buffer works in the desired ranges of pH and ionic strength and does not negatively interact with the desired antigenic factors, the HO-apa or its supporting material. Exemplary buffers for use in this invention include, without limitation, phosphate, borate, acetate, carbonate, Tris, and ammonium buffers.

The adsorbent is subsequently packed into a column and the antigenic factors adsorbed thereto are eluted from the support at nearly neutral pH and in a buffered saline at a high ionic strength greater than 200 mM. Desirably the elution is performed at a temperature range of 1° to 15° C. The elution is preferably accomplished at a pH of between about 6.0 to 9.0 with a buffered saline. Also preferred is a temperature of approximately 4° to 8° C. The saline may be composed of any of the salts usually applicable in the field, and well known to the one of skill in the art. Exemplary salts include, without limitation, Na, Ca, K, Mg, ammonium salts in the soluble form of their chlorides or sulphates.

In the most preferred embodiment of the invention phosphate buffers at only two pH levels and only two dilutions per pH are used as a standard set, applicable for the washing and elution steps, as well as any additional steps in the purification and separation method of the present invention. Use of this simple buffer results in less preparation and manipulation and permits rapid performance of the steps of the method, considerably reducing the risks of destabilization of the factors and contamination. Furthermore, phosphate buffers are very compatible with HO-apa, which also contains phosphate groups.

In a preferred embodiment of the invention therefore, the HO-apa support to which the desired antigenic factors have been adsorbed is extensively washed firstly with buffer $A_1$ (phosphate 10–15 mM, pH 5.5–7.0) and secondly with buffer $A_2$ (phosphate 50–300 mM, pH 5.5–7.0) at higher ionic strength. The antigenic factors are then eluted together by applying buffer $b_2$ (phosphate 100–500 mM, pH 7.2–8.0) supplemented with NaCl (0–700 mM) and the active protein factors are pooled.

In one embodiment of this invention only the first protein peak is pooled to avoid major contamination with endotoxins. To avoid contamination from remaining cells or germs of *B. pertussis* after elution, the pooled fractions are subjected to a conventional sterile filtration.

The method of the present invention thus results in a mixture of the two desired antigenic factors in one solution. These factors in solution are characterized by a purity level of at least 30%. Typically the purity level is greater than 50%. In the solution, the factors have a specific concentration of greater than 50 mg/l for PT and/or greater than 200 mg/l for FHA as determined by specific immunoassay employing antibodies prepared in goats and rabbits immunized with the purified antigenic factors. For the techniques involved in these immunoassays, see Y. Sato et al, *Infect. Immun.*, cited above. The level of residual endotoxins in the solution containing the factors isolated by the method of the present invention is less than $5 \times 10^6$ endotoxin units per mg protein, as determined by conventional limulus amoebocyte lysate tests. These tests are known to those of skill in the art and commercially available.

The purity of these partially purified factors and the yields obtained offer important advantages over mixtures of these antigens resulting from other purification processes known to the art. Particularly, this mixture contains partially purified PT and/or FHA free of smaller fragments resulting from proteolytic events.

Also according to the practice of the present invention, the antigenic factors in the solution described above can be further purified from remaining proteins, lipids and other contaminants. Additional purification steps of the present invention include two subsequent chromatography steps. These steps may be performed, without the need to separate the two factors from the solution.

While the chromatography steps may be performed in any sequence following the conditions provided herein, a preferred embodiment of this invention is described below. This preferred embodiment avoids such time comsuming steps, as desalting, dialysis or concentrating, and reduces the risk of residual contamination from the solvent system of the first chromatography.

According to this invention, one of the chromatographic steps, preferably the first in sequence, involves loading the partially purified antigens in the above solution, at neutral or slightly alkaline pH ranging between about 6.0 to 9.0, and high ionic strength, preferably between 0.2 to 1.5 M, on a common support.

Exemplary supports for use in this step of the invention include, without limitation, cellulose, agarose, dextran, acrylic and other polycarbohydrates and their crosslinked and otherwise modified derivatives or porous resins or inorganic supports to which apolar ligands are bound in a sufficient quantity to give the carrier a hydrophobic character. The apolar ligands may be any aromatic or linear, branched or cyclic aliphatic compound containing no other polar or reactive group, such as the one involved in the bond with the support. It will be clear to one skilled in the art that the kind of apolar group selected, and the volume and the degree of substitution on the support are parameters determining the capacity of each final support to adsorb the desired antigens.

In a preferred embodiment of the invention the support for the first purification step is a common polymeric matrix to which apolar ligands are bound as substituted or unsubstituted phenyl, alkylphenyl, or linear aliphatic groups containing from two to 26 carbon atoms. Some commercially available carriers for this purpose are, e.g. Butyl-TSK, or Octyl-TSK (Merck), or Phenyl Sepharose (Pharmacia Fine Chemicals), or Butyl Sepharose (Pharmacia Fine Chemicals).

In a most preferred embodiment of the invention the support for the first purification step is selected from those characterized by greater rigidity or crosslinkage, e.g., TSK, which enables faster purification by better flow characteristics. In a most preferred embodiment, the presence of aliphatic ligands, such as butyl or octyl, on the support allows the most efficient binding and purification of the antigenic factors.

This support is further characterized by a capacity to bind simultaneously and completely the two antigens upon exposure to high ionic strength. Under conditions of high ionic strength, e.g. more than 0.2 M, the antigens appear in a more apolar form.

The buffer systems used in the chromatographic steps recited below may be any of those commonly used for the treatment of biological factors, provided they have the desired indicated ranges of pH and ionic strength and do not have negative interactions with the desired antigenic factors nor with the adsorbent. Exemplary buffers for such use include, without limitation, phosphate, acetate, carbonate, trisethanolaminomethane and ammonium buffer systems. For low ionic strength, concentrations of buffering salt are kept low; for high ionic strength, buffer salt concentrations are high, or, preferably, extra non-buffering salts are added to the system. These salts may be any of those usually applicable in the field, and well known to one of skill in the art, e.g. Na, Ca, K, Mg, ammonium salts in the soluble form of their chlorides or sulphates. In the most preferred embodiment of the invention, phosphate buffers at only two pH levels and only two dilutions per pH are used as a standard set, as described above and in Example 2.

The antigens adsorbed onto this carrier are then washed to remove most endotoxins and remaining minor impurities with a neutral to slightly alkaline (pH 7.0 to 9.0) buffered salt solution. Preferably the buffered salt solution B2 is used for the washing of the support.

The two antigens are eluted together by using an acidic buffer (pH range of 5.0 to 7.0) at a low to medium ionic strength, e.g., 10 mM to 300 mM, supplemented with a detergent. Preferably, the buffer A2 supplemented with a detergent is used for the elution of the two antigens. The detergent may be any water-soluble non-ionic detergent. In a preferred embodiment the non-ionic detergent is an ethoxylated fatty acid alcohol, e.g., Tween series (ICI, UK), Triton X-series (Rohm and Haas, USA), Berol series (Berol, Denmark) or Marlipal series (Huls, Germany), and is added to the buffer in about 0.5 to 25%. The most preferred detergents are Berol 185 (Berol) and Marlipal 24/80 (Huls), which enable a fast elution with as little as 0.5 to 5.0% detergent. After this elution step, the fractions containing the antigens are pooled.

The other chromatography step useful in this method involves loading the pooled antigenic solution from the extraction step, or preferably, the pooled antigenic fraction from the first chromatographic step at slightly acidic pH (pH 5.0 to 7.0) and low ionic strength (10 mM to 200 mM) onto a second carrier able to retain both antigens. This step allows removal of the detergent from the preceding step.

The second carrier capable of retaining both antigenic factors is preferably a hydroxyapatite carrier. Exemplary carriers for this use include hydroxyapatite, pure, supported on, or entrapped in, another carrier material, or a Cibacron-blue modified gel support commonly used in the biological and biochemical field. Other carriers described above which are able to adsorb both desired antigenic factors at slightly acidic to neutral pH (pH 5.0 to 7.0) and low ionic strength (10 mM to 200 mM) are useful in this method. The preferred support is a commercially available adsorbent with good flow characteristics and mechanical resistance, that retains both antigens when contacted at pH 5.0 to 7.0 at low ionic strength. Examples of such carriers are, without limitation, HA Ultrogel (IBF, France), Trisacryl-Blue (IBF, France), Blue Sepharose gel (Pharmacia, Sweden), Affigel Blue (BioRad, USA) and equivalent thereof. For this step of the purification Trisacryl Blue is the most preferred adsorbent.

The supported antigens are thereafter washed with a buffered solution at low ionic strength, and eluted together with a neutral to slightly alkaline buffered solution (pH 6.0 to 9.0) at high ionic strength greater than 200 mM. Preferably the buffered solution A2 is used for the washing and the buffered saline solution B2 is used for the elution of the antigens. Alternatively, the two antigens are eluted with a linear gradient of NaCl in a phosphate buffer. The active fractions are identified by specific immunoassays [see Sato et al, cited above] and pooled.

At this stage the desired antigenic fractions are obtained as a mixture of two highly purified antigens in a single solution. Typically, only the 5 protein subunits which constitute pertussis toxin and the 220 KDa FHA species are detected by SDS-gel electrophoresis. FHA is often obtained by other purification methods as a mixture of smaller protein species, which correspond to degradation products of the 220 kd species. See, e.g., T. L. Cowell et al, in "Bacterial Vaccines", Vol IV:3-71–379, Robbins, Hill, Sadoff eds., Thienne-Stratton, New York (1982). Thus, an additional advantage of the present invention is the purification of the intact FHA species from other degradation products.. The endotoxin content of the purified antigens, measured by the limulus amoebocyte test, is less than 10 endotoxin units per mg protein.

In this form the antigens can be used in a toxoiding reaction, i.e. using formalin, glutaraldehyde, hydrogen peroxide, tetranitromethane or other inactivating agents. This mixture can also be used as a bulk purified antigen stock solution for the preparation of vaccines employing techniques normally applied in the vaccine art. For example, the mixture may be subjected to conventional procedures for sterile filtration, detoxification, correction of concentrations and addition of adjuvants normally used in the administration of vaccines, such as aluminum hydroxide, aluminum or calcium phosphates. Alternatively the solution can be employed for vaccines in combination with other antigens or toxoids against the same or other diseases.

If, however, ratios for the two B. pertussis antigens other than the ratio existing in the resulting solution mixture are desired or only one single antigen is desired for use as a vaccine, diagnostic agent or the like, the two factors can readily be separated from each other without cross contamination on the basis of their molecular weights. Conventional techniques for separation of PT from FHA in the mixture include exclusion chromatography on a typical gel support, a technique well known to one of skill in the art. Such exclusion chromatographic gels are generally commercially available, e.g. Sephacryl gel (Pharmacia). For example, if separation of the two pure factors is desired, the final antigen pool can be loaded on Sephacryl S200-HR gel, after corrections for the protein concentration, and the antigens subsequently eluted from this gel using the solvent system B1 (phosphate buffer 10–100 mM, pH 5.5–8.5 containing 300–700 mM NaCl).

Thus the method of the present invention described herein is characterized by a number of advantages in contrast to the methods of the art. For example, unlike prior methods of purification of either of these two antigens, the method of the present invention unexpectedly enables the selective extraction of both the PT and FHA antigens from B. pertussis culture by a single adsorption step, and without prior removal of cells and debris by centrifugation. The method of this invention thereby avoids the use of specific, and not readily available, human or animal affinity ligand modified supports used frequently in prior art methods.

The method of this invention is also performed easily and rapidly because large volumes of fermentation culture need not be handled. The method of the present invention also contributes to the quality and purity of the final antigenic factors in that it may be performed rapidly and, if desired, under fully sterile conditions. External contamination from contact with the atmosphere or from foreign biological material, such as affinity ligands, and internal contamination from thermal denaturation or degradation is maximally avoided by this process.

Also surprising is that, in contradiction to the expectations of the one skilled in the field, and to the observations of Svoboda et al and Sato et al, cited above, this process eliminates the difficulties of flow impediment by adhering cells or poor mechanical resistance or interference of UV monitoring by adsorbed nucleic acids. The use of hydroxyapatite as the first step in the overall purification without prior centrifugation of the culture liquid is believed to be a major advantage of this process.

Another advantage of the method of the invention is its use of commonly available synthetic chromatographic supports. Such synthetic supports provide to the method and the resulting purified antigenic factors the advantages of improved sterilization and safety for human use. Surprisingly, some chromatographic supports previously described for the purification of PT or FHA, or for the selective adsorption of one of the two antigens without major retention of the second factor, were found satisfactory in the method of this invention to adsorb and elute the two desired factors together when working in a specific range of pH and ionic force provided by this method.

The methods of the present invention also reduce the manipulation of the active fractions after pooling, thereby reducing the risk of contamination. Because of its numerous advantages, the process of the present invention is useful in the isolation and purification of each of the factors, PT or FHA, separately or in combination.

The following examples are illustrative only and do not limit the scope of the present invention.

EXAMPLE 1

Extraction Method

A culture of B. pertussis phase I, Tohama is fermented in modified Stainer-Scholte medium according to the methods and Conditions described in EPA 239,504, which is incorporated herein by reference.

After fermentation is complete, the culture broth is cooled to between 1°–10° C., and the pH adjusted to about 6.2 with phosphoric acid. The preservative, sodium thimerosal, is added to the broth to a final concentration of 0.1 g/l.

35 g (3%v/v) of sterilized HA-Ultrogel support is added to the broth and left in contact with the broth overnight with gentle stirring. After allowing the support-adsorbed antigen to sediment, it is separated from the bulk of the culture broth and washed repeatedly with phosphate buffer (pH 6.2, 10 mM).

After a first washing, the adsorbent is packed into an Amicon column (type G90). A second washing is then applied with phosphate buffer (100 mM, pH 6.2) and the antigenic factors are eluted together by applying phosphate buffer (pH 7.6, 200 mM), supplemented with NaCl (500 mM).

Figure 1:
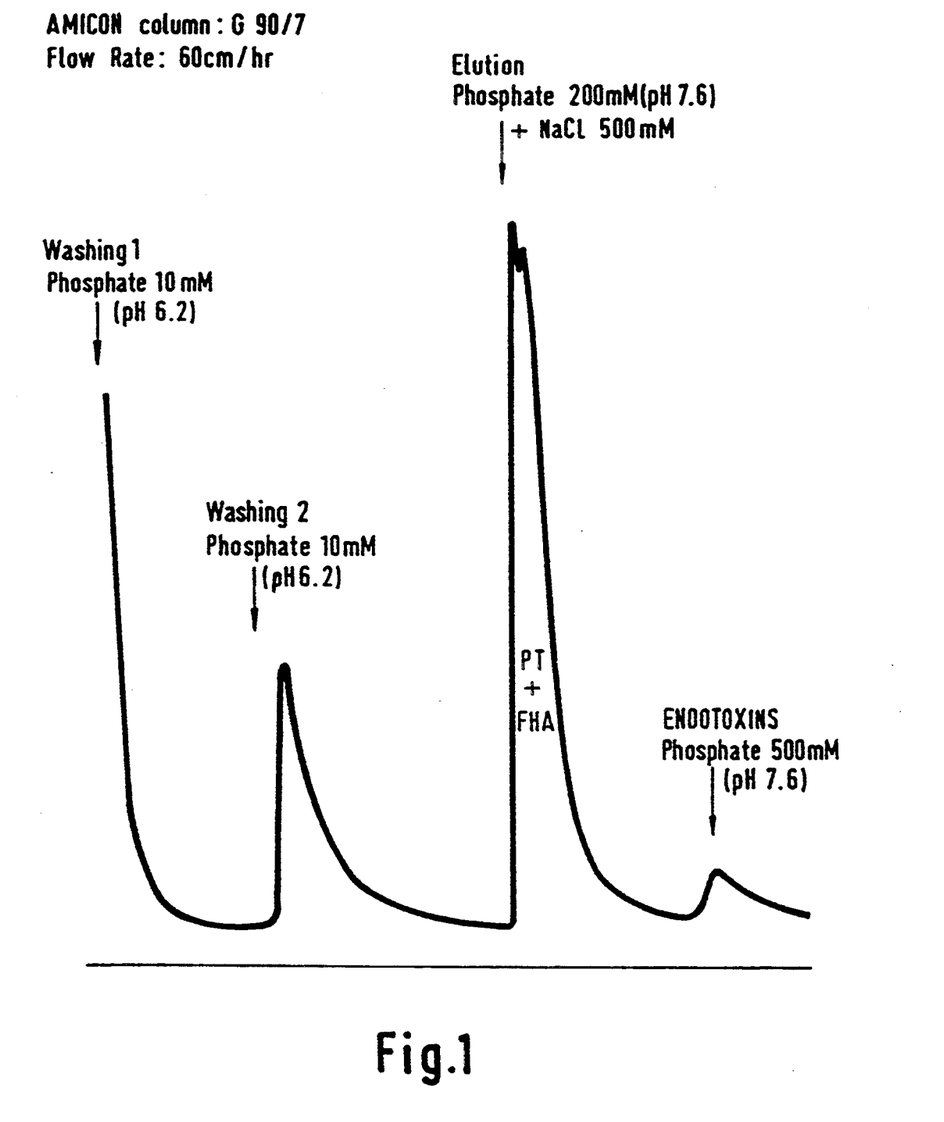
FIG. 1 is an elution profile recorded at 280 nm of the protein peak obtained after performing the method of the invention as described in Example 1.

The active protein peak is pooled. A typical elution profile is illustrated in FIG. 1 (U.V. monitoring at 280 nm).

This process thus results in one solution containing a mixture of PT and FHA in partially purified form. This solution is then subjected to sterile filtration.

EXAMPLE 2

Purification Method

The partially purified antigenic factors from the solution of Example 1, dissolved in phosphate buffer (pH 7.6, 200 mM), supplemented with NaCl (500 mM) are loaded without any other treatment onto a Butyl-TSK carrier equilibrated previously with the same buffer.

Figure 2:
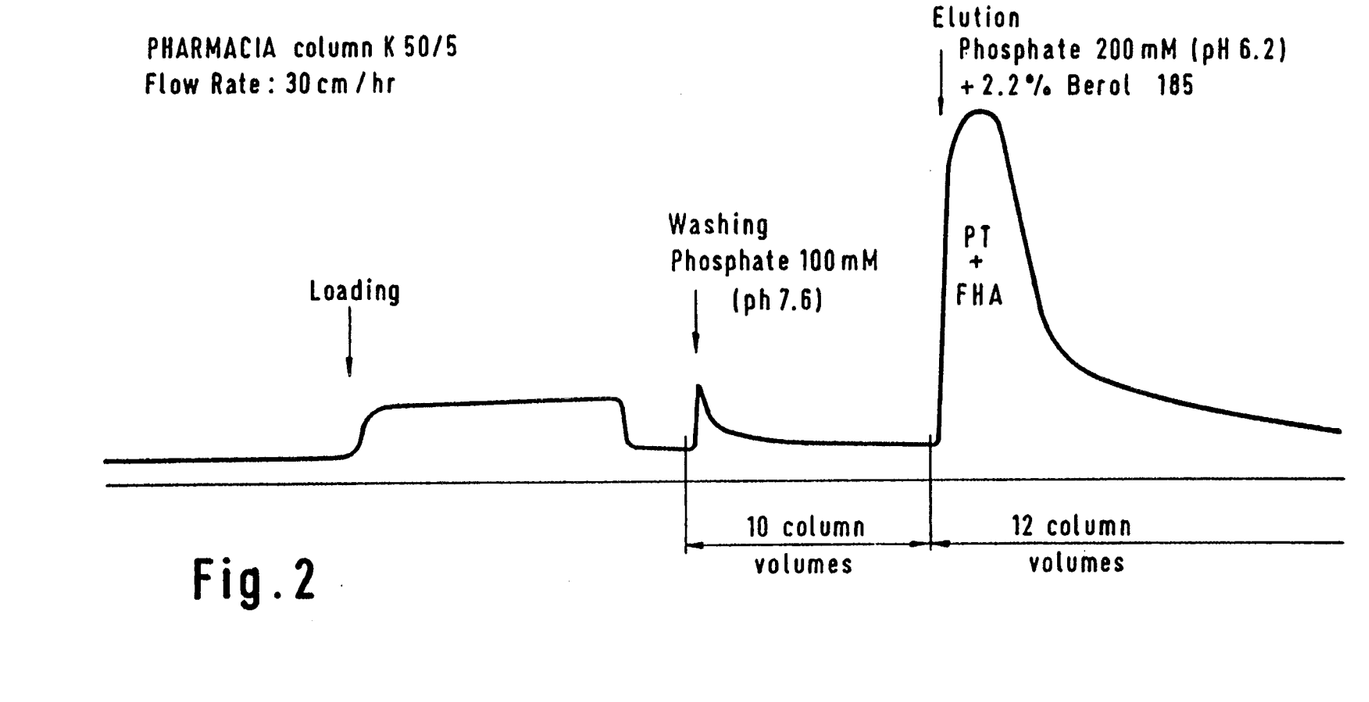
FIG. 2 is an elution profile recorded at 280 nm of the protein peak from the first of the two chromatographic steps of the method of this invention as described in Example 2.

The adsorbed antigens are washed with the same buffer as above, whereby the endotoxin level is further decreased by a factor of from about 50 to about 1000. The antigens are co-eluted with phosphate buffer (200 mM, pH 6.2) to which 2.2% Berol 185 detergent (Berol, Denmark) is added, and the active fractions pooled. A typical elution profile is provided in FIG. 2 (U.V. monitoring at 280 nm).

Figure 3:
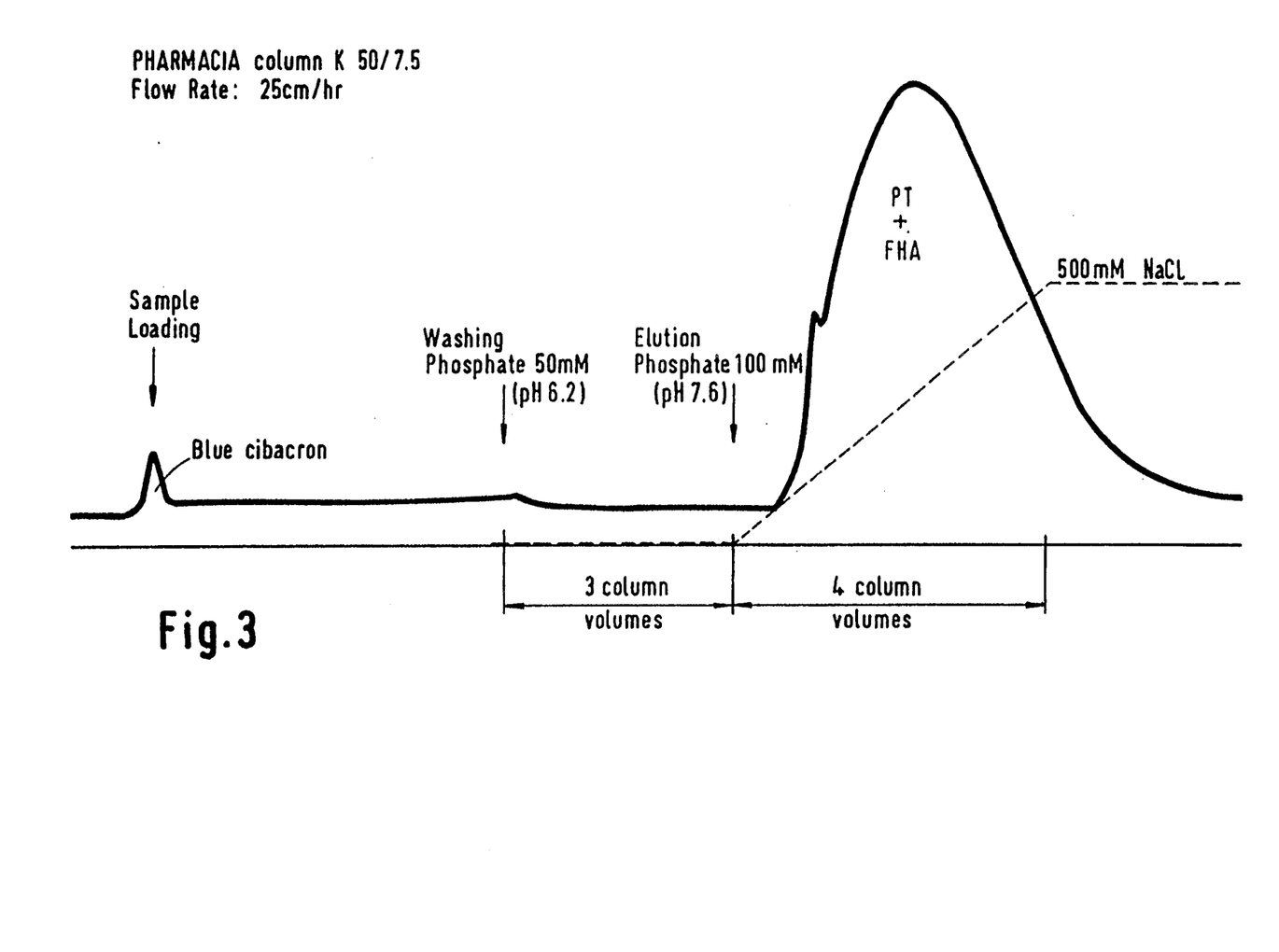
FIG. 3 is an elution profile recorded at 280 nm of the protein peak from the second chromatographic step of the method of this invention as described in Example 2.

The pool from this first chromatographic purification step is then diluted with pyrogen free water to a concentration of less than 100 mM, and loaded on Trisacryl Blue equilibrated with phosphate buffer (50 mM, pH 6.2). This adsorbent is washed with the same buffer to remove all traces of detergent. The desired antigens are thereafter eluted together with a linear gradient (0 to 500 mM) of NaCl in phosphate buffer (100 mM, pH 7.6) and the active fractions are pooled. A typical elution profile is provided in FIG. 3 (U.V. monitoring at 280 nm).

The resulting solution contains the two desired biological factors, PT and FHA, in very pure form.

EXAMPLE 3

Separation of Antigens

When the separation of the two antigens in the solution of Example 2 is desired, a size exclusion chromatography is accomplished on Sephacryl S-200 HR using a phosphate buffer (50 mM, pH 7.6) supplemented with NaCl (500 mM). A protein concentration of 1.5 to 3.0 mg/ml in the pooled fractions of the Trisacryl Blue column is preferred for an easy separation of antigens on the Sephacryl S200-HR gel.

Figure 4:
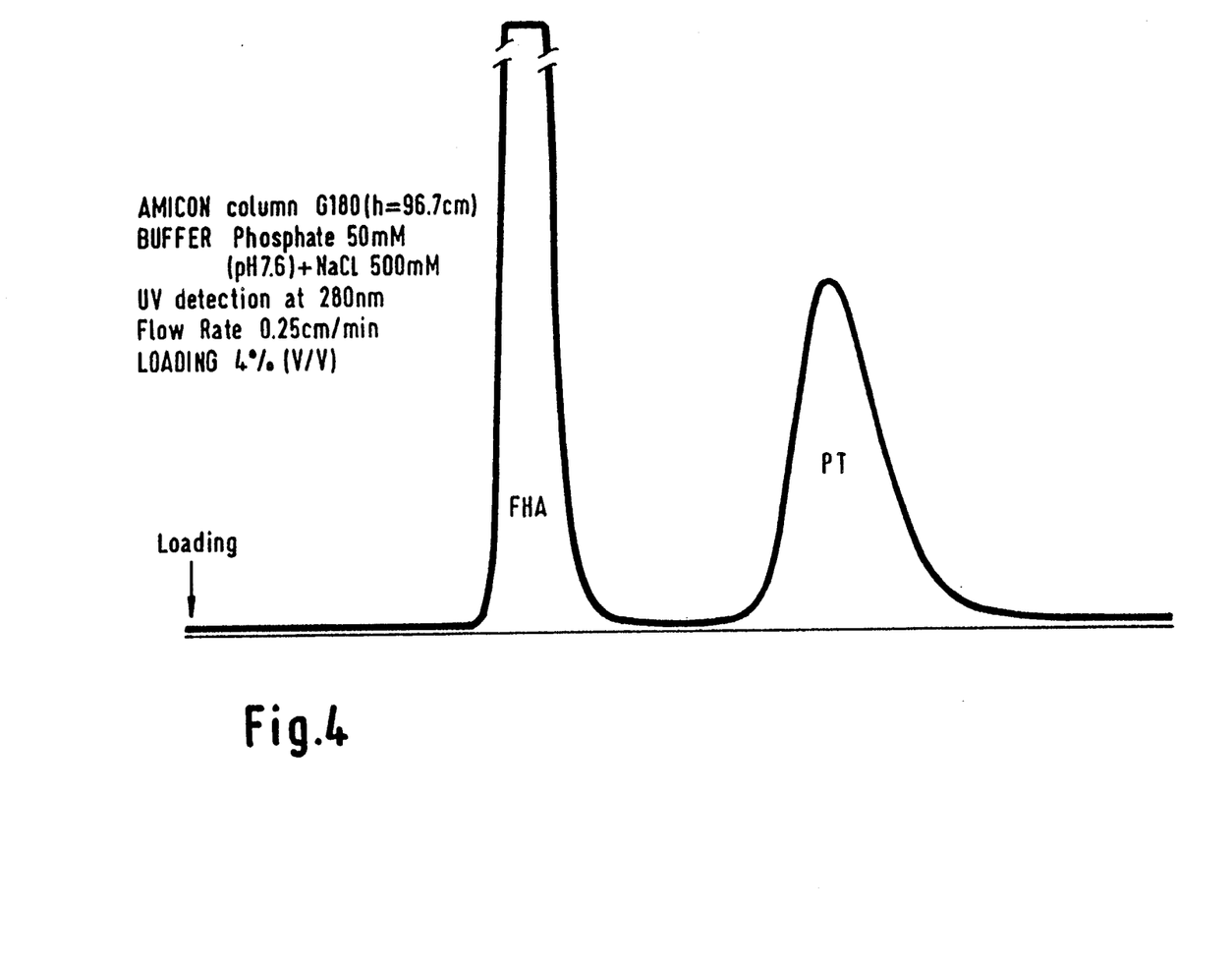
FIG. 4 is an elution profile recorded at 280 nm of the antigenic factors PT and FHA separated by size exclusion chromatography as described in Example 3.

From this gel, PT elutes at less than 0.1 kd and FHA elutes at greater than 0.3 kd. A typical elution profile is provided in FIG. 4 (U.V. monitoring at 280 nm).

The highly purified antigens obtained can now be treated fully separately for the preparation of toxoids and/or for the further development of immunogenic preparations, or be mixed up in any ratio with each other or with other antigens, toxoids or immunogenic factors before doing so.

EXAMPLE 4

Vaccine Preparation

The purified antigens can then be submitted to inactivation by chemical agents, i.e. formalin, glutaraldehyde, hydrogen peroxide, tetranitromethane or other inactivating agents, to eliminate toxic properties of PT. Optionally, FHA, which has no toxic properties by itself and is substantially free of PT contamination, can be used without inactivation treatment. Thus, inactivated PT and FHA or treated FHA are then processed to remove inactivating agents and combined to the desired proportions and mixed with the adjuvant, i.e. aluminum hydroxide, aluminum or calcium phosphate.

Thus, the products and processes of the present invention are characterized by the advantages of simplicity of the process steps and of the techniques involved, common availability of the materials and the apparatus used, rapid processing (e.g., less than two days from the end of the fermentation till the final pure antigens) and easy scale up for industrial production, while providing for good yields, protection against external contamination, and purity by specific selectivity for the antigens rather than unwanted substances from the fermentation broth.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

We claim:

1. A method for the purification of pertussis toxin (PT) and/or filamentous hemagglutinin antigen (FHA) from a B. pertussis fermentation broth or cell free culture supernatant containing at least one of the said toxin and antigen, which method comprises:
   contacting the said broth or supernatant with a hydroxy-apatite containing adsorbent for a time sufficient to adsorb the said toxin and/or antigen at a pH below 7.0 at which both PT and FHA are adsorbed; and eluting a first mixture, containing at least one of the said adsorbed toxin and/or antigen, from the said adsorbent with eluant at pH which both PT and FHA are eluted.

2. A method according to claim 1, wherein the said adsorbent has a specific density of at least 1.15.

3. A method according to claim 1, wherein the said adsorbent comprises hydroxyapatite on a porous or semi-permeable carrier.

4. A method according to claim 3, wherein the said carrier is selected from the group consisting of silica, alumina, other inorganic porous supports, organic resins and bio-gelling supports.

5. A method according to claim 1, wherein the said adsorbent is added to the said broth in an amount of at least 0.5 grams of hydroxyapatite per liter of the said broth.

6. A method according to claim 1, wherein the said adsorbtion time is between 5 minutes and 30 hours.

7. A method according to claim 1, further comprising washing the said adsorbent with the said toxin and/or antigen adhered thereto with a buffered solution at an ionic strength of less than 200 mM.

8. A method according to claim 1, wherein the said eluting step is performed with a buffer under conditions of pH ranging from 6.0 to 9.0, and at an ionic strength of more than 200 mM.

9. A method according to claim 1, wherein the said first mixture comprises pooled fractions corresponding to the first protein peak to elute.

10. A method according to claim 1, further comprising the steps of subjecting the said first mixture to two sequential chromatographic columns, one of the said columns comprising an apolar-ligand chromatography column, and eluting from the second chromatographic column a second mixture comprising PT and/or FHA substantially free from endotoxins and other proteinaceous materials.

11. A method according to claim 10, wherein the said apolar ligand chromatography column comprises a support to which apolar ligands are bound in a sufficient quantity to give the support a hydrophobic character.

12. A method according to claim 11, wherein the said apolar ligand comprises an aromatic or linear, branched or cyclic aliphatic compound containing no group capable of reacting with the bond between the ligand and the support.

13. A method according to claim 12, wherein the said apolar ligand support comprises a polymeric matrix to which is bound substituted or unsubstituted phenyl, alkylphenyl, or linear aliphatic groups consisting of 2 to 26 carbon atoms.

14. A method according to claim 11, wherein the said support is selected from the group consisting of cellulose, agarose, dextran acrylic polycarbonates, and crosslinked and modified derivatives thereof.

15. A method according to claim 10, wherein the apolar-ligand chromatography step comprises (a) loading the column at a pH greater than 6.0 and an ionic strength greater than 0.2 M, and/or (b) washing the loaded column under conditions of pH greater than 7.0 and/or (c) eluting the toxin or antigen from the column together in an acidic buffer under conditions of pH lower than 7.0 and ionic strength lower than 300 mM in the presence of a water-soluble, non-ionic detergent.

16. A method according to claim 10, wherein the said apolar-ligand chromatography column is the first of the two columns.

17. A method according to claim 10, wherein the said second chromatography step comprises loading the eluted mixture from the first column at a pH lower than 7.0 and ionic strength lower than 200 mM onto a support capable of binding both PT and FHA, and eluting from the said support under conditions of pH greater than 6.0 and ionic strength greater than 200 mM a mixture of the said PT and/or FHA substantially free from endotoxin and other proteinaceous materials.

18. A method according to claim 1, wherein said fermentation broth or cell free culture supernatant contains both PT and FHA, which further comprises separating PT from FHA by size exclusion chromatography.

19. The method according to claim 4, wherein the organic resins and bio-gelling supports are elected from the group consisting of acrylic resins, vinylic resins, agarose, cellulose and mixtures thereof, and are optionally rigidified or structuralized by cross-linking.

20. A method according to claim 11, wherein the said support consists of porous resins or inorganic supports.

21. A method according to claim 10, wherein said fermentation broth or cell free culture supernatant contains both PT and FHA, which comprises the additional step of separating PT from FHA by size exclusion chromatography.

* * * * *

UNITED STATES PATENT AND TRADEMARK OFFICE
CERTIFICATE OF CORRECTION

PATENT NO. : 5,391,715

DATED : February 21, 1995

INVENTOR(S) : Capiau et al.

It is certified that error appears in the above-identified patent and that said Letters Patent is hereby corrected as shown below:

On column 3, line 47, change:
"*Vaccine*, :199-207", to
--*Vaccine*, 5:199-207--.

Column 15:

In Claim 15, line 32 change:
"and/or (c) eluting the toxin or antigen", to
--and/or (c) eluting the toxin and/or antigen--.

Signed and Sealed this

Fourth Day of July, 1995

Attest:

BRUCE LEHMAN

*Attesting Officer*  *Commissioner of Patents and Trademarks*